United States Patent [19]

Schlichting, Jr.

[11] 4,092,221

[45] May 30, 1978

[54] APPARATUS FOR BIOLOGICALLY MONITORING AIR QUALITY

[76] Inventor: Harold E. Schlichting, Jr., 151 S. Ridge St., Port Sanilac, Mich. 48469

[21] Appl. No.: 566,915

[22] Filed: Apr. 10, 1975

[51] Int. Cl.² .............................................. C12K 1/00
[52] U.S. Cl. ................................................. 195/127
[58] Field of Search ................ 195/127, 103.5 R, 139, 195/142

[56] References Cited

U.S. PATENT DOCUMENTS 3,690,837  9/1972  Witz et al. ............................. 195/127
3,741,877  6/1973  Shaufus et al. ................ 195/103.5 R Primary Examiner—Raymond N. Jones
Assistant Examiner—Robert J. Warden

[57] ABSTRACT

A method and apparatus to indicate air quality and locate sources of air pollution utilizing selected living indicator organisms. Air is drawn through a divided chamber or a series of chambers containing indicator organisms. A comparison is made of the growth and physiological health of the organisms in purified air, i. e., where the particulate matter and chemicals have been removed by a series of filters, and of those organisms in air from which only the particulate matter is removed.

1 Claim, 3 Drawing Figures

APPARATUS FOR BIOLOGICALLY MONITORING AIR QUALITY

BACKGROUND OF THE INVENTION

To my knowledge no air biological monitoring chamber has ever been constructed or used by anyone anywhere prior to my construction of an Air Biomonitor. A Biomonitor for water quality studies, first constructed in October, 1973 by the petitioner, was first marketed in March, 1974. During this period plans were drawn up by the petitioner for an air biomonitoring chamber as herein described and illustrated.

It has been known for nearly 25 years that lichen growth and health can assess many air pollutants and the value of these living organisms rather than man-made instruments for assessing sulfur dioxide levels is that they are inexpensive and give quick results. Lichens are especially useful in forestry to assess where conifers should be planted since conifers are affected by the same sulfur dioxide levels that cause lichen cover to decline. The possibility of transplanting healthy lichens into areas suspected of being polluted, and monitoring physiological parameters such as respiration and photosynthesis, to give a rapid indication of pollution levels is obvious. The rate of accummulation of air pollutants in the lichen, moss or algal plants can be determined by means such as biomass decrease or increase per unit time, pigment analysis, rate of respiration or photosynthesis and heavy metal or isotope accummulation.

Effects of air pollutants besides hydrogen fluoride (HF) and sulfur dioxide ($SO_2$) on lichen growth which have been studied to some degree are copper (Cu), Cadmium (Cd), iron (Fe), lead (Pb), manganese (Mn), nickel (Ni) zinc (Zn), cesium-137 ($Ce^{137}$), strontium-90 ($Sr^{90}$), ionizing radiation, smoke, dusk, fertilizer spray or dust, fungicidal sprays and weed killers. The effect of ozone ($O_3$), nitrite ($NO_2$), and hydrogen sulfide ($H_2SO$) is not well understood at this time. These lichens are very sensitive to fluorides: *Evernia prunastri, Parmelio caperta* and *Usnea barbata*. Chlorophyll a & b are broken down and fluorides inactivate the whole pigment system just as occurs in higher plants.

Aerial or subaerial algae would also be ideal as indicators of air pollution because of ease of handling, range of species specific sensitivity which is greater than in higher plants and much quicker physiological responses to air chemistry than occur in high plants. Many of the cortecolous, lithophilous and epiphytic algae, lichens, liverworts, fern gametaphytes and mosses are ideally suited as air biological monitoring organisms. Using both pollution tolerant and pollution sensitive species would be best for air quality indication.

Ecological and taxonomic studies of lichens have been conducted in various parts of the world for over 100 years. Jones' (1952) suggestion that lichen vegetation could assess air pollution levels was supported by Fenton (1960) while Trass (1971) was able to correlated a mean annual sulfur dioxide ($SO_2$) value with his lichen index "P" to cover sulfur dioxide levels from less than 10 to 300 mg/m$^3$. By transferring lichens grown on bark discs from clear air areas to polluted air areas, Brodo (1961, 1967, 1971), LeBlanc and DeSloovey (1970) and Skye (1968) demonstrated the sensivity of specific lichens to air pollutants. Nash (1972) correlated the growth of various lichen communities in relation to a zinc factory and found *Lecanora conizaloides* most tolerant and *P. perlata* least tolerant. A number of European studies taking months and even years to complete have related lichen growth to industrial areas. Identification and mapping, usually difficult for experts, probably cannot be done by a layman without advanced study. The most recent review of the research conducted to date and the value of lichens in air pollution monitoring is presented in "Air Pollution and Lichens" by B. W. Ferry, M. S. Baddeley and D. L. Hawksworth, Eds. (Athlone Press, University of London, England. 1973) and "A Guide to Air Quality Monitoring with Lichens" by W. C. Dension and S. M. Carpenter (Lichen Technology, Inc., P. O. Box 369, Corvallis, Oregon, 97330. 1973).

Algae as indicators of air quality was first suggested by the applicant in 1967 using aerial algae and in 1974 using subaerial algae. Especially suitable as test organisms in the Air Biomonitor are the microalgae found in both aerial and subaerial habitats such as species of *Chlamydomonas, Chlorella, Chlorococcum, Chlorosarcina, Chlorosarcinopsis, Gloeocystis, Chlorhormidium (Klebshormidium), Nannochloris, Pleurococcus, (Protococcus), Stichococcus, Trebouxia, Trentepholia, Chroococcus, Gloeocapsa, Nostoc, Oscillatoria, Schizothrix,* and *Scytonema* and the diatoms- *Navicula* and *Nitzschia.*

References cited to show status of prior art:
Brodo. 1961. Ecology 42: 838–841.
—. 1966. Bryologist 69: 427–449.
—. 1971. Conservationist, N. Y. 26: 22–26.
Fenton. 1960. Irish Nat. J. 13: 153–159.
Jones. 1952. Rev. Bryol. & Lichen. 21: 96–115.
LeBlanc & DeSloover. 1970. Canadian J. Bot. 48: 1485–1496.
Nash. 1972. Bryologist 75: 315–324.
Schlichting. 1969. J. Air Pollution Control Assoc. 19(12): 946–951.
—. 1975. Brit. J. Phycology. 10(2): In Press.
Skye. 1968. Acta Phytogeographica Sueciea. 52: 1–123.
Trass. 1971. "Paleotolerantnost lishainikov" in Vimba, E. (ed.) Mater Vi Simpos Mikol. i Likenal Pribalt. Respubl. 1: 66–70 Riga.

The Drawings

DETAILED DESCRIPTION

Figure 3:
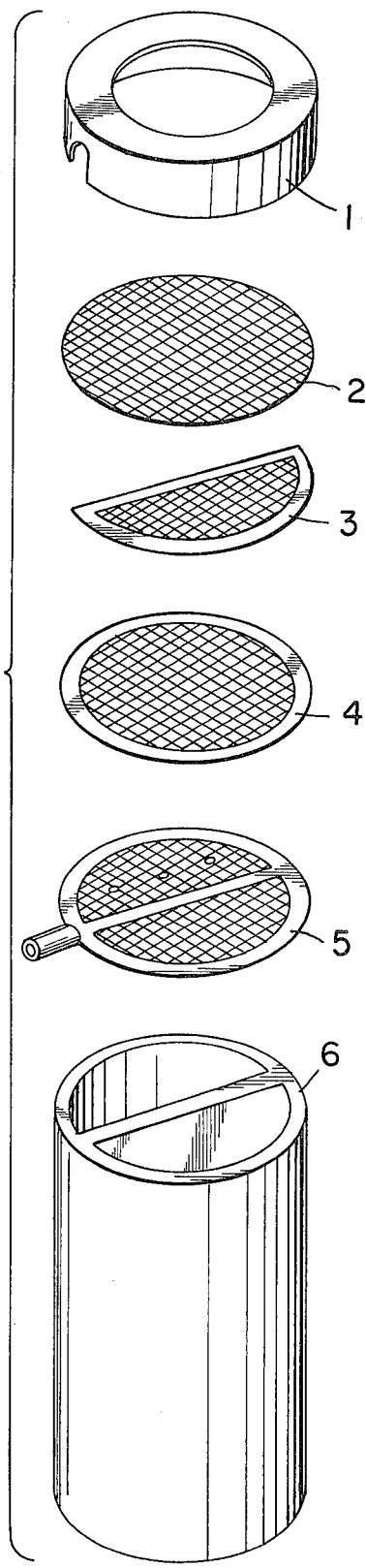
FIG. 3 is an exploded view of a biological air monitoring chamber (Air Biomonitor) showing the essential features of this Invention.

This invention concerns an apparatus of two or more chambers (divided tubes or separate tubes) through which air is drawn at known rates over test organisms. As shown in FIG. 3 air is drawn first through 2 a filter foam disc to remove large particulate matter from the entering air, 3 a semi-bonded carbon filter disc on the control sections to remove chemicals from the air, 4 a membrane filter disc removing all particulate matter larger than 0.2 to 1M$\mu$ from all sections of the chamber or tubes, 5 a porous water filter which provides humidity to all sections and scrubs the air clean of chemicals on the control sections tubes whereas openings in the water filter over the experimental sections allow chemicals to enter. An extension of the porous water filter is attached to a water reservoir tube. The chamber is sealed to render it airtight and watertight to a pump and motor with one or more flowmeters placed in line to measure the air drawn through the sections of the chamber.

Figure 1:
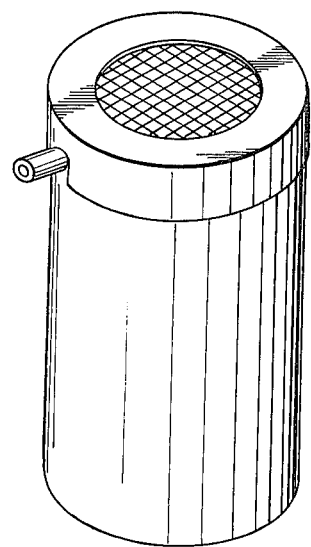
FIG. 1 is a perspective view of the biological air monitoring chamber (Air Biomonitor).
Figure 2:
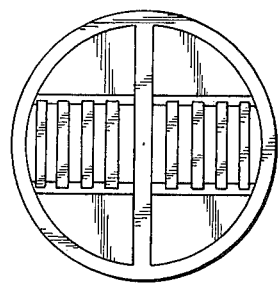
FIG. 2 is a median cross sectional view showing the interior of the chamber containing slide holders and slides.

FIG. 2 shows placement of slides of test organisms. Such organisms as aerial or subaerial algae, bacteria, fungi, lichens, moss and fern gametophytes may be placed on clear ribbons, threads of plastic, glass and even spider webs as well as glass slides. The growth rate, physiology and morphology of these test organisms will indicate air quality or the degree of air pollution, levels of pollutions in general (mixtures of gases or aerosols) or specific pollutants ($CO_2$, $SO_2$, $O_3$) after exposure to the air in the Biomonitor for specified periods of time, i.e., several hours for bacteria to a month or so for lichens. Air quality may be determined biologically by comparing or contrasting the changes in the growth per unit time (biomass), physiology or morphology of the test indicator organisms within the control and experimental sections of the Biomonitor.

SUMMARY OF INVENTION

It is now known that some living plants and animals can indicate air quality just as some indicate water quality and this invention uses a divided chamber containing test organisms through which air is drawn at known rates. The organisms in the control sections have purified air (series of filters previously described) passing over them while the experimental sections have passing through them air essentially like that surrounding the chamber. The difference in growth rate and physiological health of the organisms in each section of the chamber essentially indicates the degree of air pollution or air quality. The importance of the Air Biomonitor is in allowing less expensive air quality studies to be conducted more easily and quickly under controlled conditions and with laymen or not highly skilled technicians for biologically monitoring air quality. Test organisms are available from Carolina Biological Supply, Burlington, N.C. 27215; BioControl Company, Port Sanilac, Michigan 48469 and Lichen Technology, Inc., Corvallis, Oregon 97330 as well as from university culture collections. A biological air monitoring chamber (Air Biomonitor)

I claim:

1. An apparatus for determining air quality comprising an air tight and water tight chamber consisting of a clear tube divided longitudinally with a control area and an experimental area, both containing test organisms and a series of filters at one end of the chamber through which air passes, said filters in the control area comprising (1) a porous water filter having an extension for attaching to a water reservoir tube on top of said chamber, thereby providing humidity to all sections and to scrub the air of chemicals (2) a membrane filter disc on top of said water filter for removing all particulate matter larger than 0.2 to 1 $M\mu$ from all sections of the chamber, (3) a semi-bonded carbon filter disc on said membrane for removing chemicals from the air and (4) a filter foam disc on said carbon filter disc for removing large particulate matter; said filters in the experimental area comprising the same in the control area except the porous water filter has openings to allow chemicals to enter and there is no carbon filter disc.

* * * * *